(12) United States Patent
Jessop et al.

(10) Patent No.: US 6,997,706 B2
(45) Date of Patent: Feb. 14, 2006

(54) FLUORIDE-RELEASING PELLET KIT

(75) Inventors: Neil T. Jessop, Sandy, UT (US); Bruce S. McLean, Sandy, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 10/888,256

(22) Filed: Jul. 9, 2004

(65) Prior Publication Data
US 2005/0196729 A1 Sep. 8, 2005

Related U.S. Application Data

(63) Continuation-in-part of application No. 10/862,201, filed on Jun. 7, 2004, which is a continuation-in-part of application No. 10/793,145, filed on Mar. 4, 2004.

(51) Int. Cl.
*A61D 3/00* (2006.01)
*A61G 17/02* (2006.01)
(52) U.S. Cl. .................. 433/3; 433/8; 433/80; 433/229
(58) Field of Classification Search .................... 433/3, 433/4, 80, 229, 8, 9
See application file for complete search history.

(56) References Cited

U.S. PATENT DOCUMENTS

| | | | |
|---|---|---|---|
| 4,175,326 A | 11/1979 | Goodson | 433/80 |
| 4,685,883 A | 8/1987 | Jernberg | 433/215 |
| 4,764,377 A | 8/1988 | Goodson | 424/435 |
| 4,861,268 A | 8/1989 | Garay et al. | 433/229 |
| 5,049,077 A * | 9/1991 | Goldin et al. | 433/229 |
| 5,074,786 A | 12/1991 | Woodward | 433/80 |
| 5,137,449 A | 8/1992 | Goldin et al. | 433/229 |
| 5,437,872 A | 8/1995 | Lee | 424/464 |
| 5,820,368 A * | 10/1998 | Wolk | 433/3 |
| 5,989,569 A | 11/1999 | Dirksing et al. | 424/401 |
| 5,993,413 A | 11/1999 | Aaltonen et al. | 604/77 |
| 6,036,943 A | 3/2000 | Fischer | 424/49 |
| 6,086,855 A | 7/2000 | Fischer | 424/49 |
| 6,106,286 A | 8/2000 | Gupta | 433/80 |
| 6,126,443 A | 10/2000 | Burgio | 433/215 |
| 6,287,120 B1 | 9/2001 | Wiesel | 433/215 |
| 6,326,022 B1 | 12/2001 | Katz | 424/435 |
| 6,343,932 B1 | 2/2002 | Wiesel | 433/215 |
| 6,435,873 B1 | 8/2002 | Burgio | 433/80 |
| 6,506,053 B1 | 1/2003 | Wiesel | 433/215 |
| 2002/0081555 A1 | 6/2002 | Wiesel | |
| 2003/0003421 A1 | 1/2003 | Bestenheider et al. | |
| 2005/0136370 A1 * | 6/2005 | Brennan et al. | 433/9 |

* cited by examiner

*Primary Examiner*—Todd E. Manahan
(74) *Attorney, Agent, or Firm*—Workman Nydegger

(57) ABSTRACT

A kit that may be used to place a dental bracket and a medicament-releasing pellet in the mouth of a patient, and methods for using such kits. The pellet is designed to provide slow release of fluoride or another medicament over a desired period of time. The kit includes a medicament-releasing pellet, a dental bracket, and a placement device. The dental bracket comprises a base and a socket. The bracket may be installed by a dental practitioner and may remain attached to the patient's tooth for up to 20 years. The placement device aids the dental practitioner in placing the bracket on a patient's tooth.

20 Claims, 6 Drawing Sheets

FLUORIDE-RELEASING PELLET KIT

CROSS-REFERENCE TO RELATED APPLICATION

This application is a continuation-in-part of U.S. application Ser. No. 10/862,201, filed Jun. 7, 2004, which is a continuation-in-part of co-pending U.S. application Ser. No. 10/793,145, filed Mar. 4, 2004. The foregoing U.S. applications are incorporated herein by reference.

BACKGROUND OF THE INVENTION

1. The Field of the Invention

The present invention relates to apparatus and methods for the slow release of a medicament, particularly but not exclusively fluoride for the improved treatment and/or prevention of dental caries.

2. The Relevant Technology

Dental caries consist of demineralization of a tooth caused by bacteria. In the early stages of caries a white spot develops on the tooth and if the disease is not halted and reversed, the enamel surface breaks down to form a lesion. This can then lead to decay and eventually, a fractured or pitted tooth. It is well known that development of dental caries may be reduced by means of various factors, such as diet and oral hygiene measures, anti-microbial treatments and the provision of fluoride to the teeth.

Current methods for administering fluoride include the fluoridation of drinking water, the ingestion of fluoride tablets, the incorporation of fluoride into mouth washes, dentifrices and foods, the topical application of fluoride solutions, gels and varnishes, and recently, the incorporation of fluoride in dental materials and special devices. These have a variable effect on caries which is unpredictable on an individual basis and is dependent on patient compliance in following the prescribed regimen.

Evidence supports the concept of frequent applications of relatively low concentrations of fluoride ions for the elimination of caries. A sustained and controlled release delivery system could help to achieve this goal. At least three general approaches have been reported for the application of sustained and controlled slow releasing systems: (1) a sustained release ingested tablet or capsule (Masuhara et al. 1985); (2) incorporation of fluoride into dental cements (McClean & Wilson); and (3) an intra-oral device attached to the teeth (Minth et al. 1983). However, each of these existing technologies has been difficult to use, unpredictable, susceptible to damage, an irritant to surrounding tissue, or unacceptable to the patient.

BRIEF SUMMARY OF THE INVENTION

The present invention is directed to a kit for use in placing a dental bracket designed to receive a medicament-releasing pellet onto a tooth of a patient. The dental bracket and pellet are designed to provide slow release of fluoride or another medicament over a desired period of time. The invention also relates to a method of using the kit to place the bracket and pellet on a patient's tooth.

According to one embodiment, the kit includes a medicament-releasing pellet, a dental bracket having a base and a socket designed to receive the pellet, and a placement device. The placement device includes a body sized and configured to be at least partially inserted into a person's mouth. The placement device further includes a protrusion disposed on the body sized and configured so as to releasably attach to the socket of the dental bracket.

The medicament-releasing pellet may have any of various shapes, such as spherical, ellipsoidal, loaf-shaped, bar-shaped, or any other shape. It is preferable that the medicament-releasing pellet have a smooth surface and no sharp edges, although this is not required. The pellet may be formed of amorphous or crystalline glass, light or chemically curable resins, thermoplastics, or other materials that may be formed into a desired shape. A medicament (e.g., fluoride) is incorporated into the forming material. One example is a phosphorus based fluoride containing glass disclosed in U.S. patent application Ser. No. 10/069,143, which was filed Feb. 14, 2002, and which is incorporated herein by reference.

The dental bracket is formed of a biocompatible material, for example plastic or a biocompatible metal, such as stainless steel or nickel-titanium. Plastics may be shaped using any known method including thermoplastic molding, thermosetting molding, and the like. When formed of metal, the device may be formed through stamping, cold forming, electro-chemical etching, or any combination thereof.

The base of the dental bracket is sized and configured to be attached to a patient's tooth. The base provides surface area in order to securely bond the bracket to a patient's tooth. According to one embodiment, the base may be flexible so as to better conform to the tooth surface. The base may be transparent or opaque. At least a portion of the base may be perforated. Perforations allow light to pass through to cure a light curable adhesive when the bracket is formed of an opaque material. Perforations also allow the adhesive to flow into the perforations, resulting in a better bond between the bracket and a patient's tooth.

According to one embodiment, the socket is sized and configured to receive a correspondingly-shaped medicament-releasing pellet. It may be formed so as to be flexible or rigid, as desired. Preferably, the medicament-releasing pellet fits tightly into the socket so as to minimize space between the pellet and the socket wall. Minimizing this space prevents food, bacteria, and other debris from lodging there and festering. The pellet may be inserted or removed by manipulating the socket with an instrument, such as a dental explorer.

The placement device of the kit is used to position the dental bracket on a tooth of a patient before bonding. According to one embodiment, the body of the placement device comprises an elongate handle, and the protrusion is located near an end of the handle.

According to one embodiment, the protrusion is male so as to mate within a correspondingly-sized and shaped female socket of a dental bracket. The male protrusion may have any of various shapes corresponding to the shape of the medicament-releasing pellet to be received by the dental bracket socket. For example, the male protrusion may be spherical, ellipsoidal, loaf-shaped, bar-shaped, or any other shape.

According to another embodiment, the protrusion includes a female cavity capable of receiving the socket of the dental bracket. As mentioned above, the socket of the dental bracket may be one of various shapes configured to receive a medicament-releasing pellet that may be spherical, ellipsoidal, loaf-shaped, bar-shaped, or any other shape. In this embodiment, the female cavity of the protrusion has a shape and size configured to receive the correspondingly shaped socket.

The placement device may be formed of any biocompatible material, such as a biocompatible metal (e.g., stainless steel or nickel-titanium) or plastic. According to one embodiment, at least a portion of the placement device may be formed of a transparent plastic material. Forming at least a portion of the placement device from a transparent material allows the dental practitioner to light cure an adhesive resin while using the placement device to hold the dental bracket against a patient's tooth in the position desired.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

I. Introduction

A detailed description of the invention will now be provided with specific reference to Figures illustrating preferred embodiments of the invention. It will be appreciated that like structures will be provided with like reference designations. To provide context for interpreting the scope of the invention, certain terms used throughout the application will now be defined.

As used herein, the term "medicament-releasing pellet" or "pellet" refers to a device for slowly releasing a medicament into the body of a patient. The device may be formed of amorphous or crystalline glass, light or chemically curable resins, thermoplastics, or other materials that may be formed into a desired shape. A medicament (e.g., fluoride) is incorporated into the forming material. Such a device is capable of slowly releasing the medicament into a patient's body when placed in the patient's mouth.

The kit of the present invention may be used for placing a dental bracket and medicament-releasing pellet in the mouth of a patient. The kit includes a medicament-releasing pellet, a bracket designed to receive the pellet, and a placement device having a handle with a protrusion sized and configured so as to be attachable to the socket of the dental bracket. The bracket comprises a base and a socket that is sized and configured to receive and hold a correspondingly-sized and shaped pellet. According to one embodiment, the bracket may be placed in the mouth of a patient as a relatively permanent fixture (e.g., up to 20 years), while the medicament-releasing pellet may be removed and replaced at regular intervals, for example once a year.

II. An Exemplary Kit

Figure 1A:
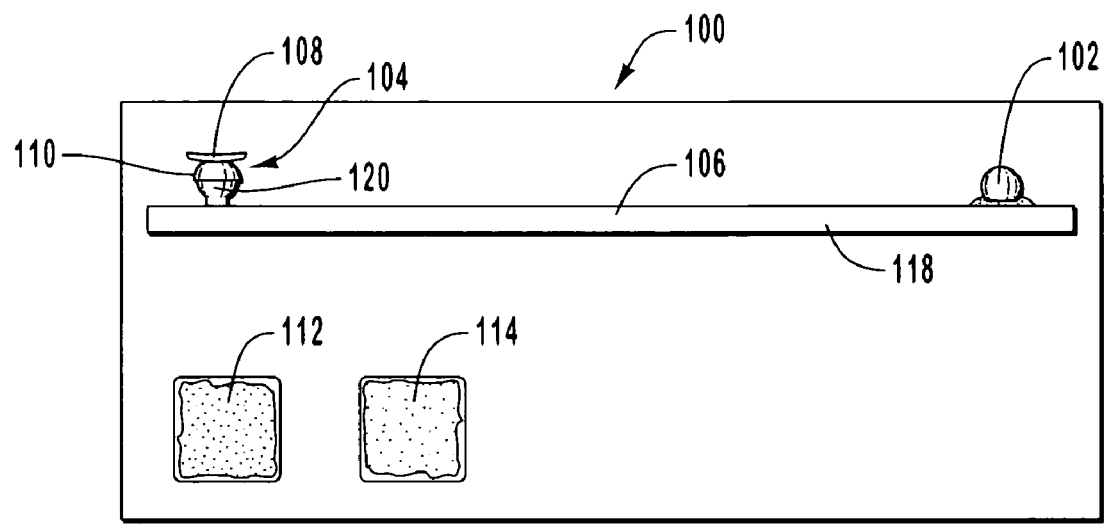
FIG. 1A is a perspective view of an exemplary kit for use in placing a dental bracket to receive a medicament-releasing pellet onto a tooth.

FIG. 1A illustrates an exemplary kit 100. The kit includes a medicament-releasing pellet 102, a bracket 104, and a placement device 106. The bracket 104 includes a base 108 and a socket 110. Exemplary kit 100 may optionally include bonding resin 112 and etch 114.

A. Medicament-Releasing Pellet

Figure 2A:
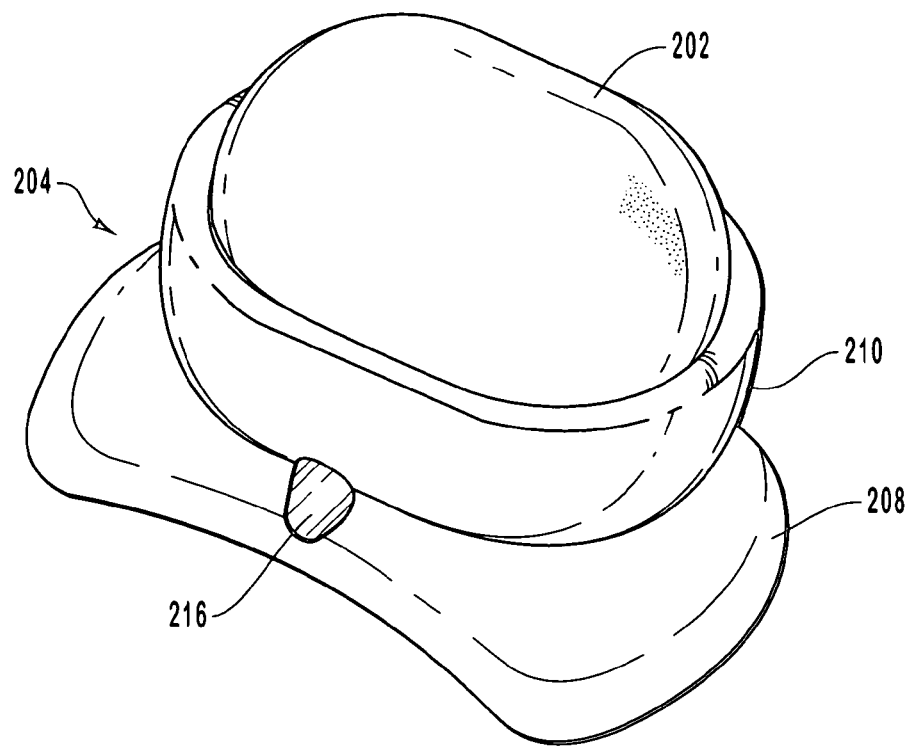
FIGS. 2A–2C are perspective views of various alternative medicament-releasing pellets and dental brackets which can be included in an exemplary kit.
Figure 2B:
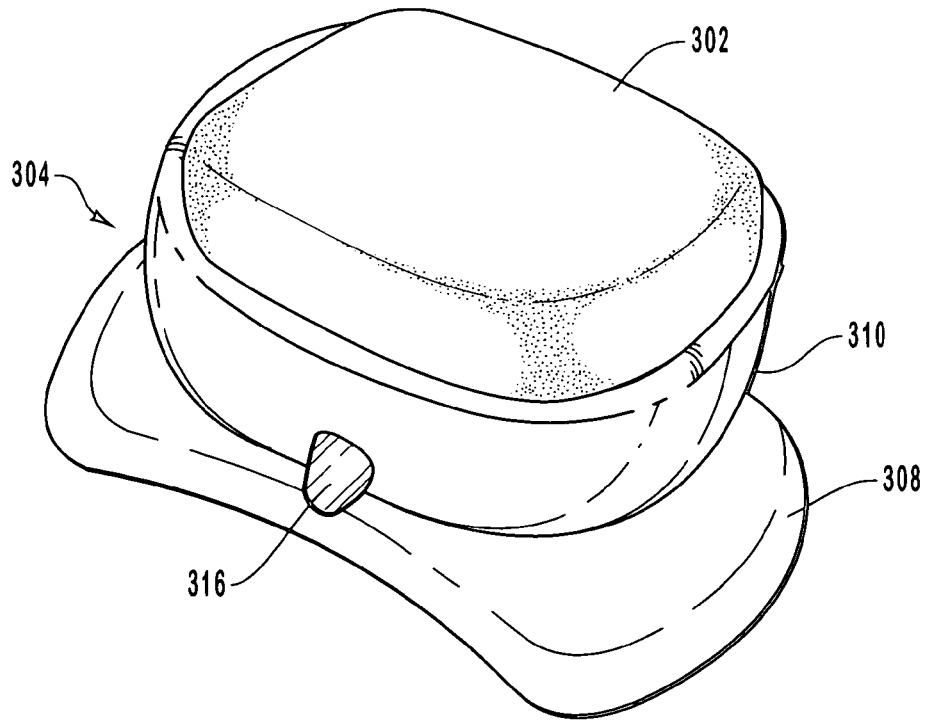
Figure 2C:
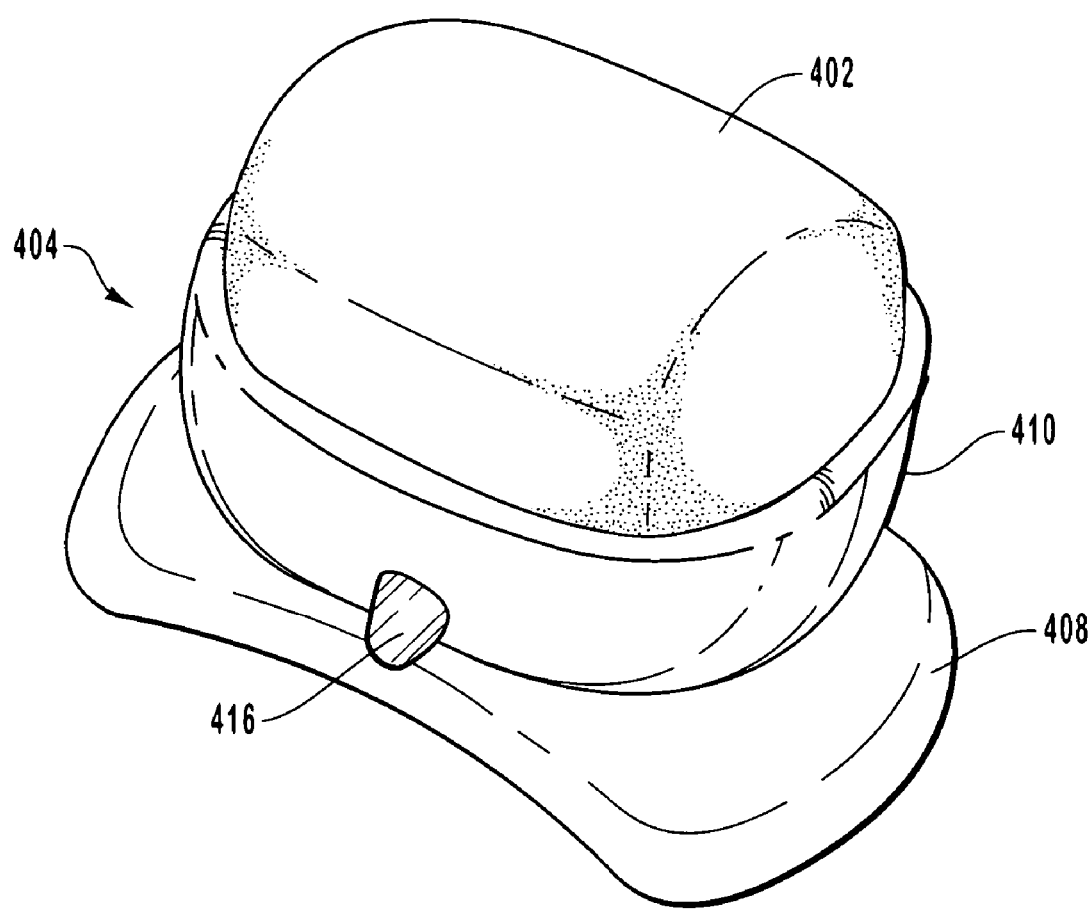

As illustrated in FIG. 1A, the kit 100 may provide the medicament-releasing pellet 102 in a configuration where it is removably attached (e.g., by rubber cement or another adhesive) to the placement device 106. The medicament-releasing pellet 102 seen in FIG. 1A has a spherical shape, although any of various other shapes, such as ellipsoidal, loaf-shaped, bar-shaped, or any other shape may be used. Examples of these alternative shapes are illustrated in FIGS. 2A–2C. FIG. 2A illustrates an ellipsoidal pellet 202, FIG. 2B illustrates a loaf-shaped pellet 302, and FIG. 2C illustrates a bar-shaped pellet 402. The medicament-releasing pellet 102 contains a medicament (e.g., fluoride) that is slowly released into the patient's body over a period of time. For example, where the medicament is fluoride, it may be slowly released over a period between 6 months and 2 years. The pellet may be formed of amorphous or crystalline glass, light or chemically curable resins, thermoplastics, or other materials. One example of a suitable glass composition is a phosphorus based fluoride containing glass disclosed in U.S. patent application Ser. No. 10/069,143, which was earlier incorporated by reference. Such a glass composition can be formed into a pellet and once placed in the patient's mouth, will slowly release the fluoride contained in the pellet over a desired period. Thermoplastics or curable resins may be desirable pellet forming materials where the medicament decomposes or is otherwise destroyed at high temperatures. In the case of fluoride, the pellet 102 may be replaced once the concentration of fluoride in the patient's mouth begins to decrease below a desired standard. For example, the pellet may be removed and replaced after a period as short as 6 months or as long as 2 years.

B. Bracket

As illustrated in FIG. 1A, the kit 100 may provide the bracket 104 in a configuration where it is removably attached to the placement device 106. The bracket 104 includes a base 108 and a socket 110. The base 108 is configured to be bonded to the surface of a patient's tooth. The base provides sufficient surface area for bonding, which results in a strong bond to the patient's tooth. The bracket 104 is intended to be attached to a patient's tooth for a relatively long period of time. Preferably, the bracket is bonded so as to remain attached to the patient's tooth for up to 5 years, more preferably up to 10 years, and most preferably up to 20 years. According to one embodiment, the base 108 is bonded to a tooth with a chemical cure or light cure adhesive resin (e.g., adhesive bonding resin 112).

In the illustrated embodiments, the socket includes one or more holes (perhaps best seen in FIGS. 2A–2C) to enable the dental practitioner to pry the medicament-releasing pellet out with a dental explorer or other instrument. The socket 110 may be formed so as to be rigid or flexible. A flexible socket 110 may be preferred where easier removal of the pellet 102 is desired. Preferably, the medicament-releasing pellet 102 fits tightly into the socket 110 so as to minimize space between the pellet 102 and the wall of socket 110. Minimizing this space prevents food, bacteria, and other debris from lodging and festering. It is intended that removal and replacement of the pellet 102 may be performed at home or in a dentist's office.

FIGS. 2A–2C illustrate alternative brackets and medicament-releasing pellets. FIG. 2A illustrates an ellipsoidal medicament-releasing pellet 202 and a bracket 204. Bracket 204 includes a base 208 and a socket 210 that is configured to receive the ellipsoidal pellet 202. The socket 210 may include one or more holes 216 to enable the dental practitioner to pry the medicament-releasing pellet 202 out with a dental explorer or other instrument.

FIG. 2B illustrates an alternative bar-shaped medicament-releasing pellet 302 and a bracket 304. Bracket 304 includes a base 308 and a socket 310. The socket 310 may include one or more holes 316 to enable the dental practitioner to pry the medicament-releasing pellet 302 out with a dental explorer or other instrument.

FIG. 2C illustrates another alternative loaf-shaped medicament-releasing pellet 402 and a bracket 404. Bracket 404 includes a base 408 and a socket 410. The socket 410 may include one or more holes 416 to enable the dental practitioner to pry the medicament-releasing pellet 402 out with a dental explorer or other instrument.

According to one embodiment, the base and socket of the bracket may be formed of a thin, resilient, biocompatible material, for example plastic, stainless steel, or nickel-titanium. A preferred material is a urethane plastic because of its exceptional compatibility with light curable adhesives. When formed of metal, the device may be formed through a combination of stamping and cold forming, while perforations (if present) may be formed by electrochemical etching. In a preferred embodiment, the base and socket are manufactured as a single piece, although they may be formed as two distinct pieces and then joined together.

C. Exemplary Placement Device

FIG. 1A illustrates a device 106 for placing a dental bracket (e.g., bracket 104) onto the tooth of a patient. Device 106 includes a body 118 and a protrusion 120 disposed on the body 118. The body 118 is sized and configured to be at least partially inserted into a person's mouth. The protrusion is sized and configured so as to releasably attach to a socket of a dental bracket used to receive and retain a medicament-releasing pellet. In the illustrated embodiment, the body comprises an elongate handle and the protrusion 120 is disposed near an end of the elongate handle 118.

The protrusion 120 illustrated in FIG. 1A is male, and configured to mate within a correspondingly-sized and shaped female socket of a dental bracket (e.g., socket 110 of dental bracket 104). As mentioned above, sockets may be configured to receive pellets which are spherical, ellipsoidal, loaf-shaped, bar-shaped, or any other shape. Accordingly, the protrusion 120 may be spherical, ellipsoidal, loaf-shaped, bar-shaped, or any other shape that is configured to mate with the socket of the dental bracket. The protrusion 120 may be flexible or rigid, as desired. A protrusion 120 which mates within the socket of a dental bracket preferably may be used with a dental bracket having a flexible socket.

Figure 1B:
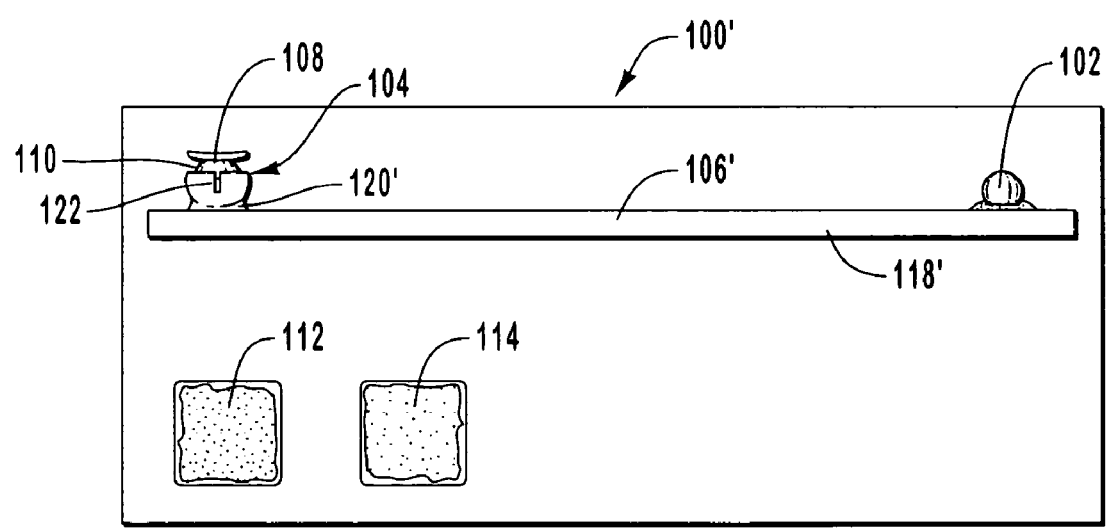
FIG. 1B is a perspective view of an alternative kit for use in placing a dental bracket to receive a medicament-releasing pellet onto a tooth.

FIG. 1B illustrates an alternative kit 100'. Kit 100' includes a medicament-releasing pellet 102, a bracket 104, and an alternative placement device 106'. Device 106' includes a body 118' and a protrusion 120' disposed on body 118' and that is configured so as to releasably attach to a socket of a dental bracket (e.g., socket 110 of dental bracket 104) used to receive and retain a medicament-releasing pellet. The protrusion 120' includes a female cavity 122 that is sized and configured to receive a socket (e.g., socket 110). The cavity 122 may be configured to receive any of the various sockets illustrated in FIGS. 1A, 2A–2C, or any other socket. A protrusion 120' which includes a female cavity 122 that receives a socket of a dental bracket preferably may be used with a dental bracket having a rigid socket. The protrusion 120' may be flexible or rigid, as desired.

The placement device (e.g., device 106 or 106') may be formed of any biocompatible material, such as a biocompatible metal (e.g., stainless steel or nickel-titanium) or plastic. According to one embodiment, at least a portion of the placement device is formed of a material transparent to curing light wavelengths. This allows light emitted by a dental curing light to pass through the placement device so as to cure an adhesive used to bond a dental bracket to a patient's tooth.

Figure 3:
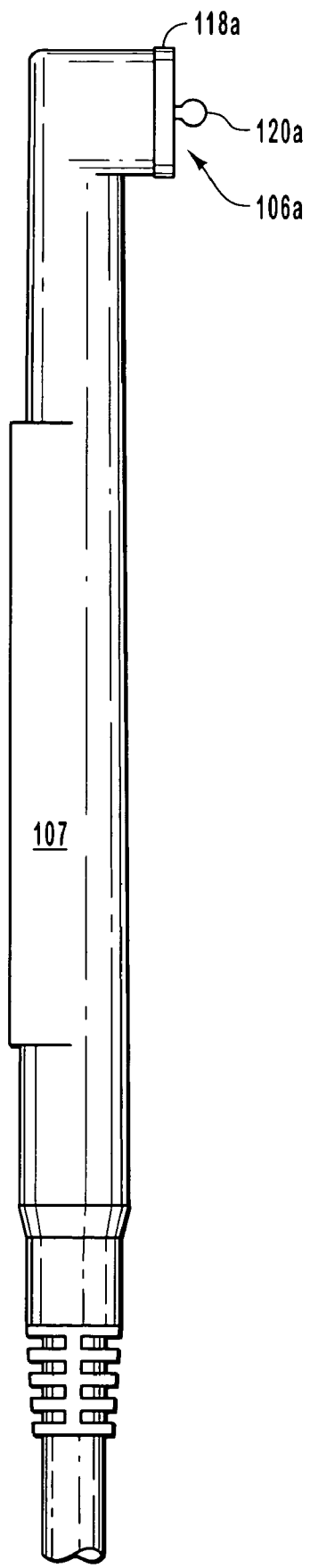
FIG. 3 is a perspective view of an alternative placement device comprising a lens attachment for a dental curing light.

FIG. 3 illustrates an alternative embodiment of a pellet bracket placement device 106a that is a lens attachment to a dental curing light 107. Placement device 106a includes a body 118a and a protrusion 120a on the body 118a sized and configured so as to be releasably attach to the socket of a dental bracket used to receive and retain a medicament-releasing pellet. Such a lens attachment 106a may be removably attachable adjacent to a light source of a dental curing light. Light generated by the dental curing light 107 is directed through the body 118a, exiting through and around protrusion 120a, which is transparent to curing light wavelengths. This allows a dental practitioner to attach the dental bracket to protrusion 120a, manipulate the body 118a by manipulating dental curing light 107, and to light cure the dental bracket to the patient's tooth in the location desired. Although protrusion 120a is illustrated as male, a protrusion including a female cavity could alternatively be used.

III. An Exemplary Method of Use

Figure 4:
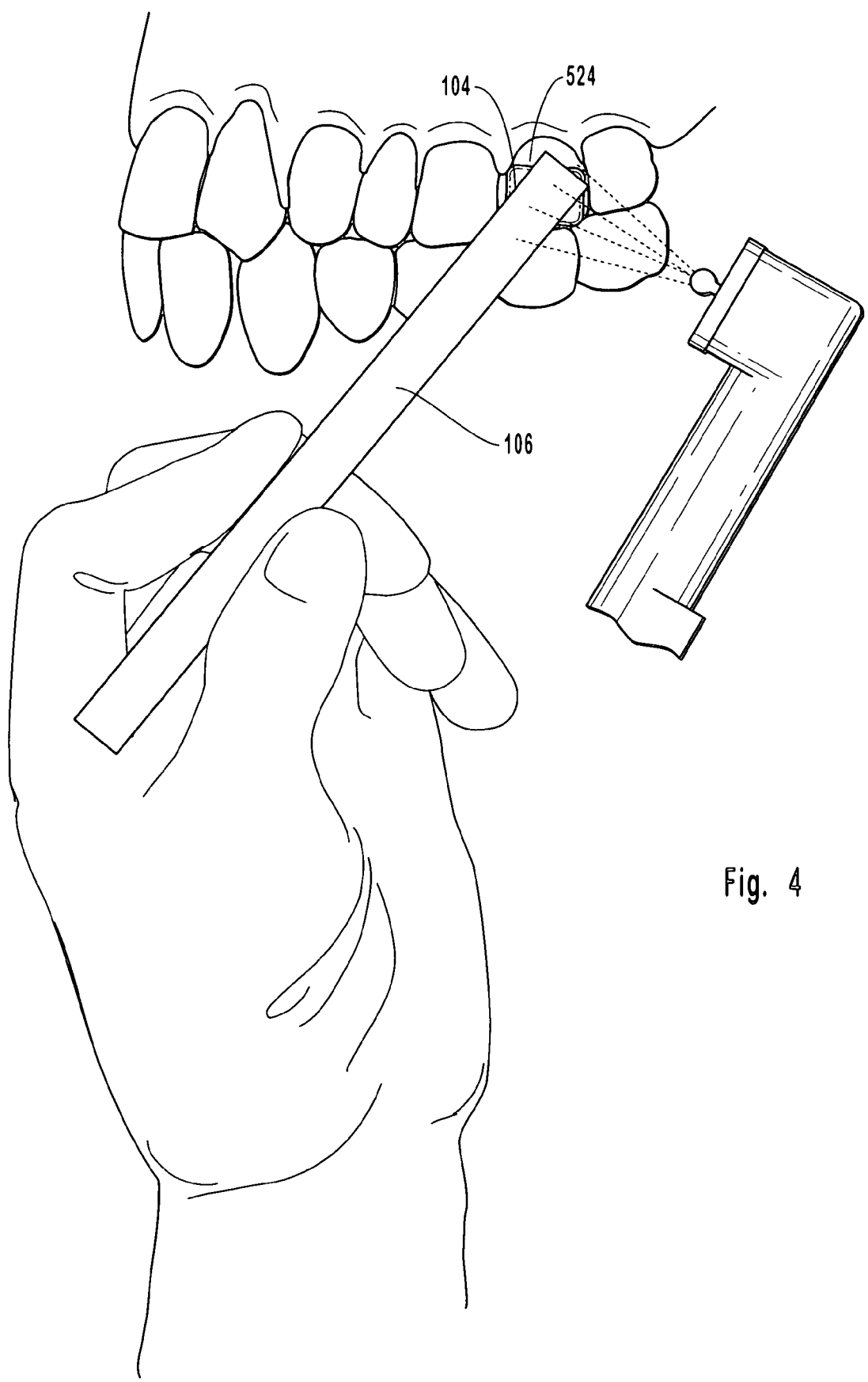
FIG. 4 is a perspective view of the dental bracket shown in FIG. 1A being positioned and bonded to a patient's tooth.
Figure 5:
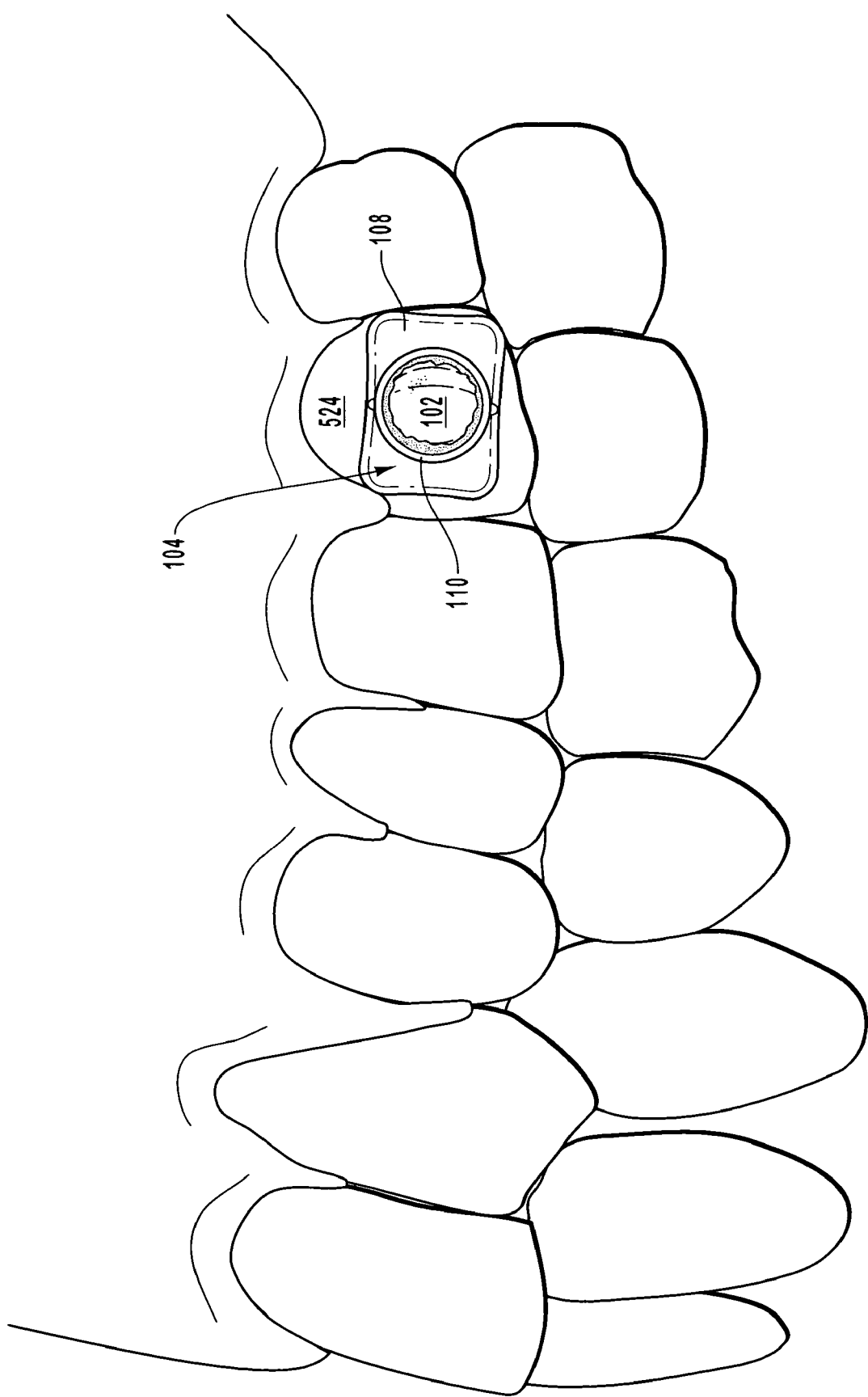
FIG. 5 is a perspective view of the medicament-releasing pellet shown in FIG. 1A being inserted so as to be received by the socket of the dental bracket bonded to a patient's tooth.

The dental bracket and medicament-releasing pellet may be attached to a patient's tooth, as illustrated in FIGS. 4 and 5. FIG. 4 illustrates positioning and attachment of the dental bracket 104 illustrated in FIG. 1A, although any of the other bracket embodiments may similarly be attached. Prior to placement and bonding of the dental bracket 104, an etch (e.g., etch 114) may be used to prepare the tooth 524 to be bonded to dental bracket 104. The dental bracket is positioned against the tooth as desired by manipulating the placement device (e.g., device 106, 106', or 106a). The bracket 104 may then be bonded to the tooth 524 with any suitable adhesive, e.g., adhesive bonding resin 112. In one embodiment, the bonding side of the base 108 may have the first part of a two-part chemical cure adhesive resin pre-applied. In another embodiment, the bonding side of base 108 may have a light activated adhesive resin pre-applied. Pre-applying either adhesive aids the dental practitioner in ease of use and placement. With the adhesive in place (whether pre-applied or applied by the dental practitioner), the dental bracket 104 is positioned on the tooth using the placement device. The base 108 provides sufficient surface area for bonding to the tooth 524. According to one embodiment, the base 108 is sufficiently curved and flexible so as to tightly fit the contour of the patient's tooth.

The medicament-releasing pellet 102 may be held within the socket 110 by a friction fit or by placing a bead of silicone resin between the socket 110 and the pellet 102. According to one embodiment, the bracket base is bonded to the patient's tooth prior to inserting the medicament-releasing pellet so as to be received by the socket of the bracket. According to another embodiment, for example when using a placement device with a protrusion having a female cavity, the medicament-releasing pellet may be inserted into the socket of the bracket prior to bonding the bracket base to the patient's tooth. As illustrated in FIG. 5, it is preferable to bond the dental bracket 104 to the patient's first upper molar, although other positions could be used. In addition, it may sometimes be desirable to install more than one device within the patient's mouth, for example, one dental bracket may be attached to each of the upper and lower first molars.

The dental bracket 104 is intended to remain installed in the patient's mouth over a long period of time (e.g., up to 20 years). The medicament-releasing pellet 102 is intended to provide slow release of a medicament (e.g., fluoride) over a period between about 6 months and about 2 years, after which time the pellet may be removed and replaced, either at home or at a dentist's office.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A kit for use in placing a dental bracket designed to receive a medicament-releasing pellet onto a tooth, comprising:
    a medicament-releasing pellet;
    a dental bracket designed to receive the medicament-releasing pellet, the dental bracket comprising:
        a base configured for attachment to a tooth surface; and
        a socket that is sized and configured to receive therein a correspondingly-sized and shaped pellet; and
    a placement device having a body sized and configured to be at least partially inserted into a person's mouth, a protrusion disposed on the body sized and configured so as to releasably attach to the socket of the dental bracket, and wherein the socket of the dental bracket is releasably attached to the protrusion of the placement device.

2. A kit as recited in claim 1, wherein the medicament-releasing pellet is substantially spherical or substantially circular.

3. A kit as recited in claim 1, wherein the medicament-releasing pellet is substantially elliptical, substantially ellipsoidal, substantially bar-shaped or substantially loaf-shaped.

4. A kit as recited in claim 1, wherein the body comprises an elongate handle, wherein the protrusion is at an end of the elongate handle.

5. A kit as recited in claim 1, wherein the protrusion is male so as to mate within a correspondingly-sized and shaped female socket of a dental bracket.

6. A kit as recited in claim 1, wherein the protrusion includes a female cavity so as to receive therein the socket of a dental bracket.

7. A kit as recited in claim 1, wherein at least a portion of the placement device is transparent so as to allow light emitted by a dental curing light to pass through the placement device so as to cure an adhesive used to bond a dental bracket to a patient's tooth.

8. A kit as recited in claim 1, wherein the protrusion is substantially spherical.

9. A kit as recited in claim 1, wherein the protrusion is substantially circular.

10. A kit as recited in claim 1, wherein the protrusion is substantially ellipsoidal.

11. A kit as recited in claim 1, wherein the protrusion is substantially bar-shaped.

12. A kit as recited in claim 1, wherein the protrusion is substantially loaf-shaped.

13. A kit as recited in claim 1, wherein the medicament-releasing pellet is releasably attached to the placement device.

14. A kit as recited in claim 1, wherein the kit further comprises bonding resin and etch.

15. A kit as recited in claim 14, wherein the bonding resin comprises a light curable adhesive resin.

16. A method of placing a bracket and medicament-releasing pellet onto a tooth, comprising:
    (a) providing a kit comprising:
        a medicament-releasing pellet;
        a dental bracket designed to receive the medicament-releasing pellet, the dental bracket comprising:
            a base configured for attachment to a tooth surface; and
            a socket that is sized and configured to receive therein a correspondingly-sized and shaped pellet; and
        a placement device having a body sized and configured to be at least partially inserted into a person's mouth, a protrusion disposed on the body sized and configured so as to releasably attach to the socket of the dental bracket;
    (b) attaching the protrusion of the placement device to the socket of the dental bracket, so that the dental bracket is releasably coupled to the placement device;
    (c) manipulating the placement device to position the dental bracket against a patient's tooth in a desired position;
    (d) bonding the dental bracket to the tooth;
    (e) removing the placement device from the dental bracket;
    (f) inserting the medicament-releasing pellet so as to be received and retained within the socket of the dental bracket.

17. A method as recited in claim 16, further comprising etching the surface of the patient's tooth prior to bonding the dental bracket to the patient's tooth.

18. A method as recited in claim 17, wherein (d) is performed prior to (f).

19. A method as recited in claim 16, wherein (f) is performed prior to (d).

20. A kit for use in placing a dental bracket designed to receive a medicament-releasing pellet onto a tooth, comprising:
    a dental bracket designed to receive a medicament-releasing pellet, the dental bracket comprising:
        a base configured for attachment to a tooth surface; and
        a socket that is sized and configured to receive therein a medicament-releasing pellet;

a placement device having a body sized and configured to be at least partially inserted into a person's mouth, a protrusion disposed on the body sized and configured to releasably attach to the socket of the dental bracket; and a medicament-releasing pellet, the pellet being releasably attached to the placement device.

* * * * *